(12) United States Patent
Nakamura (10) Patent No.: US 9,175,255 B2
(45) Date of Patent: Nov. 3, 2015

(54) METHOD OF SEPARATING CELLS AND SEPARATION APPARATUS

(75) Inventor: Chikashi Nakamura, Tsukuba (JP)

(73) Assignee: NATIONAL INSTITUTE OF ADVANCED INDUSTRIAL SCIENCE AND TECHNOLOGY (JP)

( * ) Notice: Subject to any disclaimer, the term of this patent is extended or adjusted under 35 U.S.C. 154(b) by 290 days.

(21) Appl. No.: 13/583,746

(22) PCT Filed: Mar. 9, 2011

(86) PCT No.: PCT/JP2011/055501
§ 371 (c)(1),
(2), (4) Date: Sep. 10, 2012

(87) PCT Pub. No.: WO2011/111740
PCT Pub. Date: Sep. 15, 2011

(65) Prior Publication Data
US 2013/0005038 A1    Jan. 3, 2013

(30) Foreign Application Priority Data
Mar. 11, 2010  (JP) .................................. 2010-054556

(51) Int. Cl.
*C12M 1/00* (2006.01)
*C12M 3/00* (2006.01)

(52) U.S. Cl.
CPC ..................................... *C12M 47/04* (2013.01)

(58) Field of Classification Search
CPC ......... C12M 47/04; C40B 30/04; C40B 30/10
See application file for complete search history.

(56) References Cited

U.S. PATENT DOCUMENTS

| 2003/0228695 A1 | 12/2003 | Nakamura et al. |
| 2007/0292946 A1 | 12/2007 | Nihei et al. |
| 2009/0082216 A1* | 3/2009 | Cohn et al. ........................ 506/9 |

FOREIGN PATENT DOCUMENTS

| JP | 2006-166884 A | 6/2006 |
| JP | 2006-246731 A | 9/2006 |
| JP | 2008-000008 A | 1/2008 |
| JP | 4051440 B2 | 2/2008 |

OTHER PUBLICATIONS

JP2006/246731, Nakamura et al., machine translation.*
Maciag et al., "Organizational Behavior of Human Umbilical Vein Endothelial Cells", The Journal of Cell Biology, 1982, vol. 94, pp. 511-520.*
International Search Report for International Application No. PCT/JP2011/05501 mailing date of Apr. 5, 2011 with English Translation.

* cited by examiner

*Primary Examiner* — Laura Schuberg
(74) *Attorney, Agent, or Firm* — Cantor Colburn LLP (57) ABSTRACT

A method and apparatus for discriminating and separating only specific cells in cell samples is provided. The cell separation operation includes inserting a needle-shaped body, on which a substance that selectively binds to a marker substance within each target cell has been immobilized, into each of the cell samples on a substrate, thereby causing the marker substance within each target cell in the cell samples to bind to the needle-shaped body through the substance that selectively binds to the marker substance, and then, pulling up the needle-shaped body. The binding force between the needle-shaped body and each target cell when the marker substance within each target cell has bound to the needle-shaped body is made greater than an adhesion force of each of the cell samples to the substrate, so that only target cells each containing the marker substance are pulled up and separated from the substrate.

14 Claims, 4 Drawing Sheets

METHOD OF SEPARATING CELLS AND SEPARATION APPARATUS

CROSS REFERENCE TO RELATED APPLICATIONS

This is a U.S. national stage of application No. PCT/JP2011/055501, filed on 9 Mar. 2011. Priority under 35 U.S.C. §119(a) and 35 U.S.C. §365(b) is claimed from Japanese Application No. 2010-054556, filed 11 Mar. 2010, the disclosure of which are also incorporated herein by reference.

TECHNICAL FIELD

The present invention relates to a method and apparatus for discriminating and separating only target specific cells among from various cells.

BACKGROUND ART

Various techniques for separating cells are known, e.g., the one for separating cells using mainly, as an index, physical properties of cells, such as, morphology, size, specific gravity, or biochemical properties of cells, etc. Among them, FACS (fluorescence activated cell sorting) and MACS (magnetic activated cell sorting) are the methods that are recently used. These methods distinguish only target cells in cell samples, using a fluorescence-labeled antibody or a magnetically-labeled antibody. In FACS, cell samples in a liquid flow are irradiated with a laser beam, and a fluorescence emitted by each cell in the cell samples is measured, thereby target cells are distinguished, and only the target cells are sorted. These methods are the ones for targeting an antigen on surfaces of a cell, and are not the ones for discriminating and separating target cells using, as a marker, an intracellular substance, such as protein, etc., produced within each target cell. In FACS, it is possible to use an intracellular protein as a marker by the method for producing a fusion protein with a fluorescence protein through gene recombination, however, genetically-modified cells cannot be used when it is intended to separate natural cells for use in transplant treatment. Further, in FACS, a highly precise control mechanism is needed for causing fluorescence measurement results to closely work with sorting, inevitably making it extremely expensive, and moreover, there has been a problem that a fluorescence-labeled antibody must be used.

On the other hand, the inventor of the present application has developed a cell-manipulating apparatus that inserts a needle-shaped body with a nano-level diameter (hereinafter, sometimes referred to as a nanoneedle), on which a gene or a gene expression-related substance has been immobilized, into a cell, and that enables observation of effects of the immobilized substance on the cell in real time, while detecting positions of the needle-shaped body within the cell based on a force response the cell exerts against the needle-shaped body (see Japanese Patent Registration No. 4051440). The inventor of the present application has further developed the technique of Japanese Patent Registration No. 4051440, and discovered that it is possible to detect a target protein in a cell by inserting a nanoneedle with a diameter of 200 nm, which has been modified by an antibody against the target protein, into the cell, and measuring a force response exerted against the nanoneedle when the nanoneedle is withdrawn from the cell (see Japanese Unexamined Patent Application Publication No. 2006-246731).

However, at the time when the above-described results were obtained, it was not conceived to apply these technologies to separation of target cells.

Patent Document 1: Japanese Patent Registration No. 4051440

Patent Document 2: Japanese Unexamined Patent Application Publication No. 2006-246731

DISCLOSURE OF THE INVENTION

Problems to be Solved by the Invention

An object of the present invention is to develop a technique of discriminating and separating only specific cells in cell samples, and it is intended to newly provide a technique for separating only specific target cells in cell samples by targeting a marker substance within each target cell which the above-described FACS cannot handle as the target.

Means for Solving the Problems

Description is made below, taking an experiment shown in FIG. 1 as an example, with respect to detection of a target substance within a cell with the above-described nanoneedle on which an antibody has been immobilized.

Figure 1:
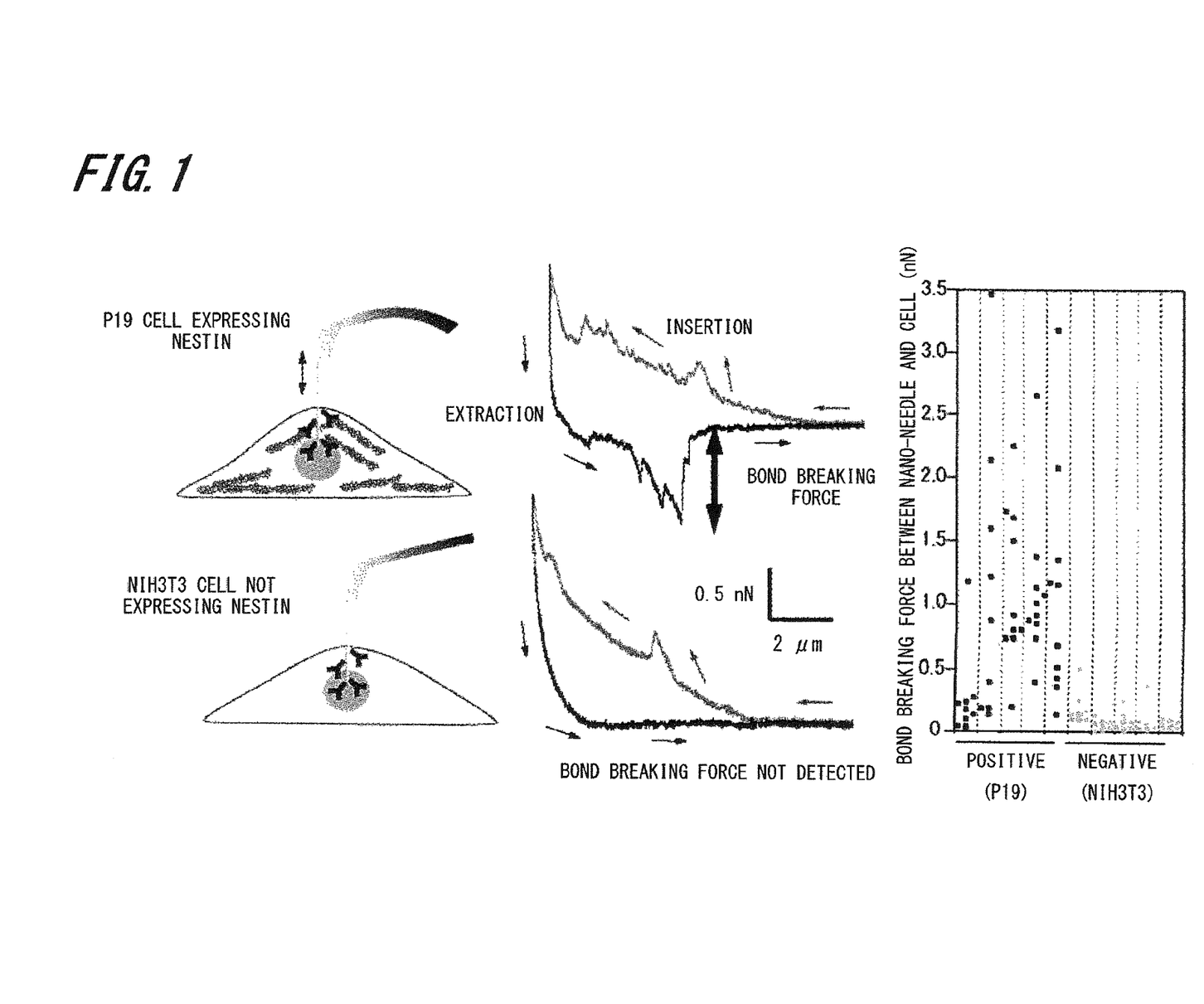
FIG. 1 illustrates results of mechanical detection of nestin within a cell with a nanoneedle that has been modified by an antibody.

FIG. 1 illustrates results of measuring force responses exerted against a needle-shaped body (nanoneedle) on which an anti-nestin antibody has been immobilized, during a period from insertion to withdrawal of the nanoneedle with respect to a P19 cell expressing nestin and a NIH3T3 cell not expressing nestin, in a detection experiment with respect to nestin as a marker for a neural stem cell. According to these results, between the nestin-expressing cell P19 and the nestin-non-expressing cell NIH3T3, the force responses at the time of withdrawing the nanoneedle are apparently different from each other, thereby enabling detection of a target substance within a cell (in this case, nestin).

The force magnitude indicated by a bold both-side arrow in FIG. 1 expresses a force required for rupturing interactions between the nestin fiber proteins and the anti-nestin antibody that has been immobilized on the nanoneedle, when the nanoneedle is withdrawn.

The value of a rapture force is a value of a force that changes depending on the withdrawal operation. When using an AFM probe having a cantilever, the value of a retraction operation is expressed as a force loading rate, which is the rate of a retraction operation multiplied by the spring constant of the cantilever. The forces described in the present specification all show values when a cantilever having the spring constant of 0.07 N/m is moved at the rate of 6 μm/sec, that is, when the loading rate is 0.4 μN/sec. On the other hand, when the force is expressed as an adhesion or binding force, it is defined as the word describing an energy amount inherent in specific binding.

The present invention was made when the inventor noticed in analyzing the rupture force as described above, that the rupture force expresses, to put it another way, the magnitude of the binding force (energy) between the nanoneedle and a cell, and that because the binding force between the nanoneedle and a cell was weaker than the adhesion force of the cell to a substrate, binding rupture was caused between the nanoneedle and the cell. Thus, the inventor noticed that if the binding force between a target cell and the nanoneedle on which an antibody has been immobilized is greater than the adhesion force of the target cell to the substrate, and the non-specific adsorption force between the nanoneedle on which an antibody has been immobilized and a cell not expressing a target protein is smaller than the adhesion force of the cell to the substrate, then, only target cells each including the target protein can be distinguished, and separated from other cells by pulling up the target cells with the nanoneedle.

In the beginning, it seemed very difficult to distinguish and separate only target cells by pulling up the target cells with the nanoneedle, if the mass of each cell itself within a liquid and viscosity resistance in the liquid when the cell pulling-up operation is carried out are considered, in addition to that the force detaching a cell from the substrate was huge such as 20-40 nN. In addition, when the needle-shaped body on which an antibody has been immobilized is inserted into a cell, the specific binding force and the non-specific adsorption force vary depending on the marker substance and its antibody, and types of cells, and the range in which the adhesion force of each cell to the substrate must be adjusted is extremely narrow.

However, the inventor of the present application dared to challenge this experiment of cell separation, and through innovative measures, such as decreasing the adhesion force between each cell and the substrate in a suitable range, controlling the dwell time of the nanoneedle in each cell, etc., finally succeeded in discriminating and separating only specific cells each containing a marker substance among from cell samples.

The followings are the inventions of the present application.

(1) A method of selectively separating cells according to an embodiment of the present invention includes inserting a needle-shaped body, on which a substance that selectively binds to a marker substance within each target cell has been immobilized, into each of cell samples on a substrate, thereby causing the marker substance within each target cell in the cell samples to bind to the needle-shaped body through the substance that selectively binds to the marker substance, and then pulling up the needle-shaped body, thereby selecting and separating only target cells each containing the marker substance. The binding force between the needle-shaped body and each target cell when the marker substance within the target cell has bound to the needle-shaped body is made greater than the adhesion force between the substrate and each of the cell samples on the substrate.

(2) The method of selectively separating cells described in (1) above, in which the binding force between the needle-shaped body and each target cell in the cell samples on the substrate when the needle-shaped body has been inserted into the target cell and the marker substance within the target cell has bound to the needle-shaped body is made greater than the adhesion force between the substrate and each of the cell samples on the substrate by increasing the binding force between the needle-shaped body and each target cell when the marker substance within the target cell has bound to the needle-shaped body and/or by decreasing the adhesion force between the substrate and each of the cell samples on the substrate.

(3) The method of selectively separating cells described in (2) above, in which the binding force between the needle-shaped body and each target cell when the needle-shaped body has been inserted into the target cell and the marker substance within the target cell has bound to the needle-shaped body is made greater than the adhesion force between the substrate and each of the cell samples by adjusting the needle-shaped body to a shape that increases a contact area of the marker substance and the needle-shape body within each target cell when the needle-shaped body has been inserted into the target cell and/or by controlling a dwell time of the needle-shaped body within each of the cell samples when the needle-shaped body has been inserted into the cell sample.

(4) The method of selectively separating cells described in (2) above, in which the adhesion force between the substrate and each of the cell samples on the substrate is decreased by treatment of the cell samples with a proteolytic enzyme and/or treatment of the cell samples with an adhesion protein inhibitor.

(5) The method of selectively separating cells described in any one of (1)-(4) above, including controlling density of a cell adhesion material to be immobilized on the substrate, controlling a suction power when suction immobilizing the cell samples on the substrate, and controlling each contact area of chambers provided in the substrate for holding the cell samples.

(6) The method of selectively separating cells described in any one of (1)-(5) above, including controlling a speed of pulling up the needle-shaped body and/or controlling a position of insertion and a frequency of insertion of the needle-shaped body into each cell sample.

(7) The method of selectively separating cells described in (3) above, in which the needle-shaped body, on which a substance that binds to a marker substance within each target cell has been immobilized, is in a cylindrical shape with an aspect ratio of 50 or above and a diameter of 300 nm or below.

(8) The method of selectively separating cells described in (3) above, in which the dwell time of the needle-shaped body, on which a substance that selectively binds to a marker substance within each target cell has been immobilized, is 1-10 sec.

(9) The method of selectively separating cells described in (6) above, in which the speed of pulling up the needle-shaped body, on which a substance that selectively binds to a marker substance within each target cell has been immobilized, is 1-500 μm/sec.

(10) The method of selectively separating cells described in (6) above, in which an insertion position of the needle-shaped body, on which a substance that selectively binds to a marker substance within each target cell has been immobilized, into a same cell sample is changed each time the needle-shaped body is inserted into the cell sample, and a frequency of insertion of the needle-shaped body into a same cell sample is 3-10 times.

(11) The method of selectively separating cells described in any one of (1)-(10) above, in which the adhesion force of each of the cell samples to the substrate is adjusted such that an adhesion force is within 500 pN-2 nN when a loading rate of the needle-shaped body, on which the substance that selectively binds to the marker substance within each target substance has been immobilized, into each of the cell samples on the substrate is 0.4 μN/sec.

(12) A method of recovering target cells, each pulled up by a needle-shaped body with the method of selectively separating cells described in any one of (1)-(11) above, by causing each of the pulled-up target cells to contact a substrate and then pulling up the needle-shaped body, in which an adhesion force of each of the pulled-up target cells to the substrate is made greater than the binding force between the needle-shaped body and the pulled-up target cell.

(13) The method described in (12) above, including controlling a contact time of each pulled-up target cell relative to the substrate, controlling density of a cell adhesion material to be immobilized on the substrate, controlling a suction power when suction immobilizing each of the pulled-up target cells on the substrate, and controlling each contact area of chambers provided in the substrate for holding recovered target cells.

(14) A method of recovering target cells, each pulled up by a needle-shaped body with the method of selectively separating target cells described in anyone of (1)-(11) above, in a liquid by increasing resistance of the liquid relative to each of the pulled-up target cells, thereby causing each pulled-up target cell to drop from the needle-shaped body, and recovering the pulled-up target cell in the liquid, the method of recovering target cells including moving the needle-shaped body holding each pulled-up target cell at a high speed in a liquid, and/or causing the needle-shaped body holding each pulled up target cell to contact a flowing liquid.

(15) The method described in any one of (1)-(14), in which a plurality of the needle-shaped bodies, on each of which the substance that selectively binds to the marker substance within each target cell has been immobilized, are arrayed, and respective needle-shaped bodies are individually inserted into the cell samples at the same time.

(16) An apparatus for selectively separating cells, including: a needle-shaped body on which a substance that selectively binds to a marker substance within each target cell has been immobilized; a substrate on which cell samples are arrayed; a positioning device to position the needle-shaped body relative to each of the cell samples arrayed on the substrate; and an operation device to insert the needle-shaped body into each of the cell samples, hold the needle-shaped body, and pull up the needle-shaped body. The adhesion force of each of the cell samples to the substrate is set smaller relative to the binding force between the needle-shaped body and each target cell when the needle-shaped body has been inserted into the target cell and the marker substance within the target cell has bound to the needle-shaped body.

(17) The apparatus described in (16) above, in which the needle-shaped body is set to a shape that increases a contact area between the marker substance and the needle-shaped body within each target cell when the needle-shaped body has been inserted into the target cell.

(18) The apparatus described in (17) above further including any one or more of: a dwell time controlling device configured to control a dwell time of the needle-shaped body, on which the substance that binds to the marker substance has been immobilized, within each of the cell samples when the needle-shaped body has been inserted into the cell samples; a pulling-up speed controlling device configured to control a pulling-up speed of the needle-shaped body; and an insertion position and insertion cycle controlling device configured to control an insertion position and an insertion cycle of the needle-shaped body relative to each cell sample.

(19) The apparatus described in any one of item 16 through item 18 above further including: a suction device configured to suction each cell sample on the substrate so as to be immobilized on the substrate; and a suction pressure controlling device configured to control a suction pressure of the suction device.

(20) The apparatus described in (17) above, in which the needle-shaped body, on which the substance that selectively binds to the marker substance within each target cell has been immobilized, is in a cylindrical shape with an aspect ratio of 50 or above and a diameter of 300 nm or below.

(21) The apparatus described in (18) above, in which the dwell time controlling device is configured to control the dwell time of the needle-shaped body in each of the cell samples at least in a range of 1-10 sec.

(22) The apparatus described in (18) above, in which the pulling-up speed controlling device is configured to control the pulling-up speed of the needle-shaped body at least in a range of 1-500 μm/sec.

(23) The apparatus described in (18), in which the insertion position and insertion cycle controlling device is configured to control an insertion position and an insertion cycle of the needle-shaped body relative to a same cell sample.

(24) The apparatus described in any one of (16) through (23) above, in which the adhesion force of each of the cell samples to the substrate is controlled such that an adhesion force is within 500 pN-2 nN when a loading rate of the needle-shaped body, on which the substance that selectively binds to the marker substance within each target cell has been immobilized, is 0.4 μN/sec.

(25) The apparatus described in any one of (16) through (24) above, further including a cell recovery device configured to recover target cells each pulled up and separated by the needle-shaped body.

(26) The apparatus described in (25) above, in which the cell recovery device is configured to cause each target cell pulled up and separated by the needle-shaped body to contact a substrate and then pull up the needle-shaped body. The adhesion force of each pulled-up target cell relative to the substrate is made greater than the binding force between the pulled-up target cell and the needle-shaped body. The cell recovery device includes a contact time controlling device configured to control a contact time of each pulled-up target cell to the substrate, and/or a cell immobilization device configured to suction-immobilize each pulled-up target cell on the substrate.

(27) The apparatus described in (25) above, in which the cell recovery device includes a moving device configured to move the needle-shaped body holding each pulled-up target cell in a liquid at a high speed, or a device to generate a liquid flow so as to contact the needle-shaped body holding each pulled-up target cell.

Effects of the Invention

According to the present invention, by causing a marker substance within a target cell to bind to a needle-shaped body on which a substance that selectively binds to the marker substance has been immobilized, and by making the binding force between the target cell and the needle-shaped body when pulling up the needle-shaped body, greater than the adhesion force between the target cell and a substrate, the target cell within which the marker substance is present is distinguished in cell samples and only the target cell is selectively pulled up. The method of selectively separating cells with such a mechanical technique is based on an unprecedented wholly new idea.

The present invention is extremely useful, for example, in the following respects.

(1) The method according to the present invention is not a method of selectively separating target cells by targeting an antigen that is present on the surface of each target cell, but can separate target cells by targeting a substance that is present within each target cell.

(2) Cells can be separated alive, without causing damages to the cells.

(3) In separation of cells, essentially, mechanical force measurement in AFM, etc. is not necessary, and separation of cells can be carried out extremely simply and inexpensively.

(4) With provision of multiple needle-shaped bodies, and by carrying out operations of pulling up cells, target cells can be separated among from a large number of cell samples, in a short period of time and efficiently.

(5) The foreign binding molecule such as an antibody, etc. is immobilized on the surface of a needle-shaped body, and the foreign molecules are not left within a separated cell, so that the operation is relatively safe.

From the points described above, the present invention has a great potential in particular as the method of separating cells in a differentiation induction process of iPS cells. Recently, since the discovery of iPS cells, while expectations for medical transplantation of cells based on embryonic cells rise, separation of target cells has become an important subject for study. In transplantation therapy to a human using iPS cells, it is conceived as that cells in the level of one million are necessary, and also, the safety of cells must be guaranteed. In iPS cells in particular, a problem has been pointed out that compared with ES cells, differentiation induction does not occur completely, and about 0.4% remains as undifferentiated cells that have a possibility of forming a post-transplantation tumor (Nature Biotechnology 27, 743-745 (2009)). The present invention can be an effective means, for example, for separating undifferentiated cells from target differentiated cells by targeting a marker protein nestin which provides evidence when differentiation induction to neural precursor cells has been carried out.

BEST MODES FOR CARRYING OUT THE INVENTION

In the present invention, a substance that selectively binds to a target marker substance present in a target cell (hereinafter referred to as a marker-binding substance) is immobilized on a needle-shaped body, and after insertion of the needle-shaped body, on which the marker-binding substance has been immobilized, into a cell on a substrate, a pulling-up operation of the needle-shaped body is carried out. At this time, in a case that the target marker substance within the target cell has bound to the needle-shaped body through the above-described immobilized substance (marker-binding substance), when the needle-shaped body is pulled up, the target marker substance within the target cell acts as a resistor that prevents the target cell from being released from the needle-shaped body, thereby generating a binding force to the target cell. Thus, it becomes possible to pull up only a target cell in which the target marker substance is present, and only target cells are separated.

The needle-shaped body used in the present invention is not limited in particular, as long as it does not damage cells in operations of insertion into each cell, pulling-up, etc., however, it is preferable that the diameter of the insertion portion to be inserted into a cell is about 100-300 nm, more preferably about 200 nm.

On the other hand, with respect to the length of the needle-shaped body, it is adequate if a sufficient length is secured in insertion into a cell, which is about 5-100 μm, preferably about 20 μm.

As the material for the needle-shaped body, for example, silicon crystal, carbon nanotube, diamond, and metallic crystals, such as, titan, zirconium, etc., and metallic oxide, such as, ZnO, etc., are cited.

On the other hand, in the present invention, a means for positioning the needle-shaped body on a cell on the substrate and then, in that position, carrying out insertion and pulling-up of the needle-shaped body is required. There is no particular limitation with respect to such means.

As the shape of the needle-shaped body, the one having a cylindrical tip, the hook-like one, the arrowhead-like one, the T-shaped one, etc. may be cited. The shape of the needle-shaped body may be appropriately selected, considering the adhesion force between cells and the substrate, damages given to the cells, etc.

In the present invention, the number of needle-shaped bodies may be one or multiple. For example, even when only one needle-shaped body is used with respect to a plurality of cell samples placed on a substrate, the needle-shaped body on which the marker-binding substance has been immobilized is inserted into each of the cell samples and the pulling-up operation is carried out, sequentially. Those cells containing the target marker substance are pulled up and separated from the substrate by pulling up of the needle-shaped body. In the above-described operation of positioning the needle-shaped body relative to each cell, inserting the needle-shaped body into the cell, and pulling up the needle-shaped body, for example, a moving means, a position controlling means and a force detection means for a cantilever of an atomic force microscope may be used.

Figure 2:
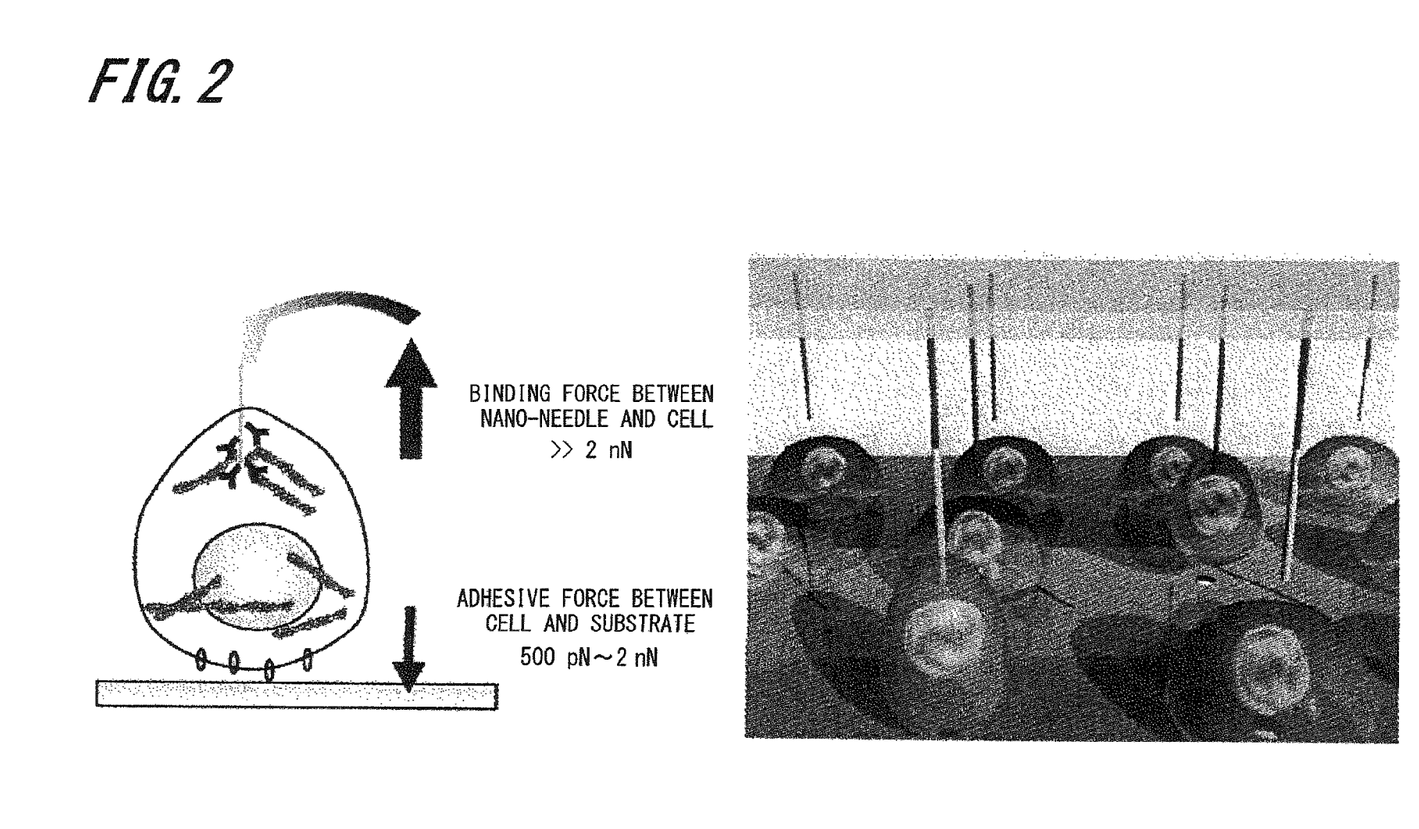
FIG. 2 is a conceptual diagram of mechanical cell separation using a needle-shaped body that has been modified by an antibody.

However, when involving numerous cell samples, as illustrated in FIG. 2, multiple needle-shaped bodies arrayed on a solid support are efficient and more preferable, for insertion to the cell samples.

The solid support on which multiple needle-shaped bodies are arrayed is preferably made of a transparent material for carrying out positioning, and the size of the solid support is about 1 cm square when 100×100 pieces of needle-shaped bodies are arrayed at intervals of 100 μm. As the device moving the solid support on which needle-shaped bodies have been arrayed closer to a cell-cultured substrate, an apparatus used in micro-contact printing, etc., may be used. However, it is needed that the part where each needle-shaped body is fixed to the solid support can be dipped into a cell culturing liquid, and that contact pressure to the solid support can be detected in order not to damage each needle-shaped body. The needle-shaped body of the above-described size is damaged by a contact force of about 1 μN, so that with respect to the solid support to which 10,000 pieces of needle-shaped bodies have been arrayed, it is preferable that the contact force of about 1 mN can be measured.

In the present invention, an intracellular marker-binding substance specific to a separation target cell is immobilized on the needle-shaped body described above. As the target marker substance, protein, glycoprotein, sugar chain, etc. may be given, however, molecules, which are relatively low molecules and monodispersed within a cell, are not preferable, and as preferable ones, proteins in a state of being bound to organelle, etc., and fibrous skeletal proteins, etc. may be cited.

Also, as the marker-binding substance which is immobilized on the needle-shaped body, various antibodies against intracellular proteins, lectins that specifically bind to sugar chains or glycoproteins, artificially-designed nucleic-acid aptamers, peptide antibodies, etc., may be given.

The method of immobilizing the marker-binding substance on the needle-shaped body is not in particular limited, and conventionally known or well known methods may be used. For example, methods such as chemical modification using a linker molecule, etc. may be cited.

As described above, in the present invention, the needle-shaped body, on which the above-described marker-binding substance has been immobilized, is inserted into a target cell and then pulled up, and the adhesion force of the target cell to the substrate at this time is made smaller than the force to rupture the binding between the marker substance within the target cell and the needle-shaped body through the above-described immobilizing substance and to make the cell to drop out, that is, smaller than the binding force between the needle-shaped body holding the marker substance and the target cell. To achieve this, although it depends on the binding force between the needle-shaped body holding the marker substance and the target cell, it is preferable to make the force to rupture the adhesion between a cell and the substrate to 500 pN-2 nN. Note that in an ordinary plastic substrate, the force to rupture the adhesion between a cell and the substrate is about 20-40 nN.

As the method of decreasing the adhesion force between a cell and a substrate, for example, cell treatment by a proteolytic enzyme such as a low concentration of trypsin, etc. or an adhesion protein expression inhibitor such as a ROCK (Rho-associated coiled-coil forming kinase) inhibitor, etc. may be cited. As the proteolytic enzyme, besides trypsin, chmotrypsin, papain, etc. may be cited, and as the adhesion protein expression inhibitor, a butyryloxazolidinone compound, a collagenase inhibitor, an elastase inhibitor, a fibronectin-binding inhibitor, etc. may be used.

The treatment by trypsin as the proteolytic enzyme is generally used, for example, for recovering adhesion-cultured cells from a substrate through decomposition of protein that works in adhesion of the cells to the substrate, and it is possible to control adhesion of cells to a substrate by trypsin treatment of the cells. By treating cells for 10 minutes with 0.01% trypsin solution, the adhesion force of 20 nN or larger can be decreased to about 2 nN, and the variation coefficient of the adhesion force can be controlled to 20% or below, so that a relatively stable weak adhesion state can be achieved.

Accordingly, in this case, if the rapture force between a cell containing a marker substance and a needle-shaped body when the marker substance within the cell and the needle-shaped body have bound together is greater than 2 nN, it becomes possible to pull up each cell containing the marker substance by pulling up the needle-shaped body.

On the other hand, depending on the types of cells or the types of marker-binding substances, the non-specific adsorption force between the needle-shaped body and each cell, which emerges when mechanically carrying out the pulling-up and separating operation with the needle-shaped body, must be considered, however, the force to rapture non-specific adsorption between the needle-shaped body and each cell is usually relatively weak as about 200 pN, and if the adhesion force with respect to each cell and the substrate is controlled to 500 pN or above, preferably to 600 pN or above, more preferably to 700 pN or above, pulling up of non-target cells, each not containing a marker substance, can be prevented.

As the means for controlling the adhesion force between cells and a substrate as described above, for example, a means for immobilizing a cell adhesion material, such as a BAM (Biocompatible Anchor for Membrane), etc., on a substrate and controlling the density thereof may be cited. When using a BAM, because the aliphatic chains of BAM molecules are inserted into the lipid membrane of a cell, thereby enabling strong holding of the cell, by controlling the density of the BAM to be immobilized on the substrate, it is possible to control the adhesion force to an arbitrary strength in the range from a few nN to 30 nN or above.

Similarly, by the method of causing cells to physically adsorb to a suction-type small orifice arrayed substrate in which small orifices are arrayed and controlling the adhesion force to the substrate, or the method of using a substrate in which chambers for increasing contact areas of cells are arrayed, it is possible to adjust the adhesion force to 500 pN or above and 2 nN or below.

One or more of the above-described cell-substrate adhesion force controlling means may be combined with the above-described cell-substrate adhesion force decreasing means, according to the above-described non-specific adsorption to be expected depending on types of cells or types of marker-binding substances.

On the other hand, it is also important to increase the force to rupture the binding between the marker substance within each target cell and the needle-shaped body through the above-described marker-binding substance and to make the cell to drop out due to the pulling-up operation of the needle-shaped body, i.e., to increase the binding force between the needle-shaped body holding the marker substance and the target cell, and with the combination of the above-described means for decreasing the adhesion force between cells and the substrate, cell separation becomes more efficient.

As the method of increasing the binding force between the needle-shaped body holding the marker substance and a target cell, for example, the method of increasing the amount of the marker-binding substance immobilized on the needle-shaped body, the method of optimizing the binding force between the needle-shaped body and a target cell by controlling the speed of pulling up the needle-shaped body, and the method of lengthening the time (dwell time) that the needle-shaped body on which the marker-binding substance has been immobilized is held within a target cell to increase the amount of the marker substance to be bound to the needle-shaped body may be cited.

Also, because whether or not pulling up of a target cell will succeed is influenced in some case by the insertion position of the needle-shaped body on which the marker-binding substance has been immobilized into the cell, it is also effective to perform the inserting and pulling-up operation to a cell a plurality of times while changing the insertion position to the cell.

The dwell time of the needle-shaped body within each target cell is dependent on the binding rate constant of the marker-binding substance to the marker substance, and in detection of a nestin with an anti-nestin antibody, the rupture force exceeding 2 nN has been measured for the dwell time of 1 sec or more. Because an extension of the dwell time that is involved in throughput of separation of cells leads to an extension of the cell processing time, the dwell time is preferably short, and one second to about 10 seconds at maximum is adequate. Similarly to the dwell time, the pulling-up speed of the needle-shaped body is preferably higher, and the pulling-up speed successful in pulling up of a cell against fluid resistance is 1-500 μm/sec.

In order to pull up a target cell, the binding force of the cell to the needle-shaped body needs to exceed the adhesion force of the cell to the substrate. When carrying out insertion to a cell multiple times, it is only necessary to succeed in pulling up the cell even once during insertion of multiple times. For example, in a case shown in FIG. 1 in which a nanoneedle on which an anti-nestin antibody has been immobilized was used for P19 cells, force detection data with respect to individual cells are shown in respective columns separated by dotted lines, and data obtained by the insertion operation of the nanoneedle repeated 10 times are all plotted in each column. Here, if the adhesion force of each cell to the substrate has been controlled to 2 nN or below, because the rapture force between nestin and the nanoneedle exceeding 2 nN has been observed at least once with respect to cells in the second to fifth columns from the left, it is indicated that the cells will be successfully pulled up.

It is preferable that the amount of the marker-binding substance to be immobilized on the needle-shaped body is large, however, because there is a possibility that the bulkiness of the immobilized substance on the surface of the needle-shaped body and the increase in the diameter of the needle-shaped body itself decrease the success rate of insertion, it is necessary to control the amount of the marker-binding substance to be immobilized on the needle-shaped body considering that the diameter of the needle-shaped body will not exceed 300 nm. The amount of the marker-binding substance to be immobilized on the needle-shaped body is adequate if the immobilization density when the marker-binding substance has been closest packed on the surface of the needle-shaped body is achieved.

The force to rupture the binding between the needle-shaped body holding the marker substance and a target cell can be increased to exceed 2 nN by these means, and cells each containing a marker substance inside can be effectively pulled up.

Each pulled-up cell can be dropped off the needle-shaped body and thereby separated and recovered, for example, with the method of bringing the cell into contact with the above-described BAM-immobilized substrate whose BAM molecular density has been controlled so as to show a cell adhesion breaking force of 30 nN or above, or the method of bringing the cell into contact with the above-described small orifice arrayed substrate in which the suction pressure has been increased, by making the adhesion force of the substrate, with which the cell is brought into contact, greater than the binding force of the cells to the needle-shaped body on which the marker-binding substance has been immobilized. As the means for increasing the adhesion force, cell adhesion materials, such as fibronectin, collagen, laminin, vitronectin, proteoglycan, nidogen, tenascin, thrombospondin, von Willebrand, osteopontin, elastin, fibrillin, tenascin, entactin, etc. may be immobilized on the substrate.

In the present invention, the operations of pulling up and recovering cells are all carried out in a liquid such as a culture solution, without exposing the cells in air. Accordingly, the substrate having cells on the surface thereof and the cell-recovering substrate are preferably adjacent to each other, and are immersed in the same liquid.

Figure 3:
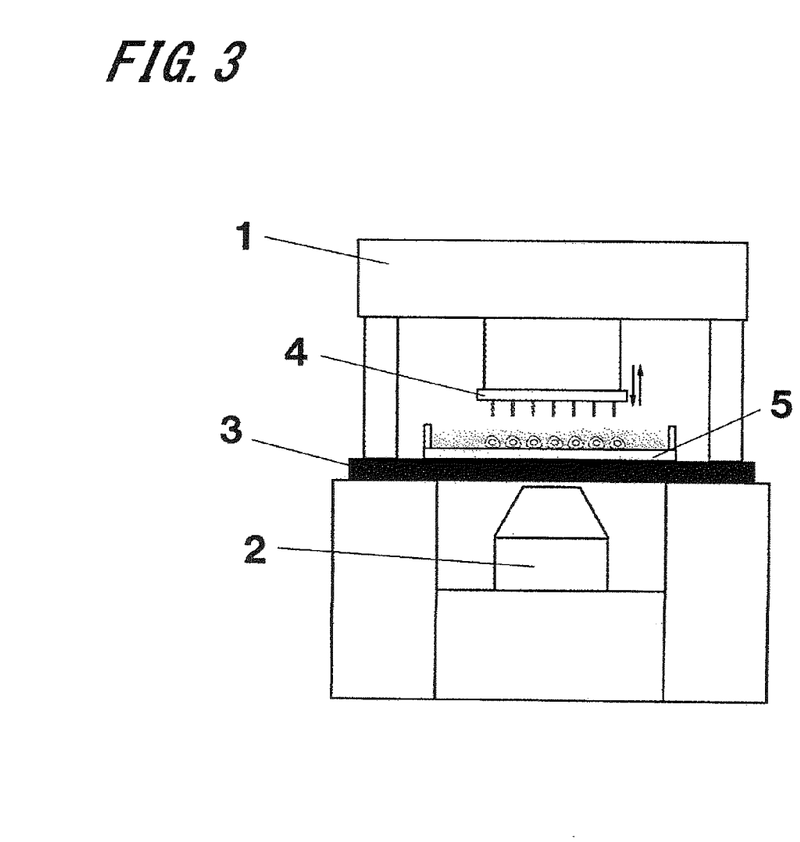
FIG. 3 illustrates an outline of a cell separation apparatus and an outline of a process of separating cells to a cell recovery substrate.
Figure 4:
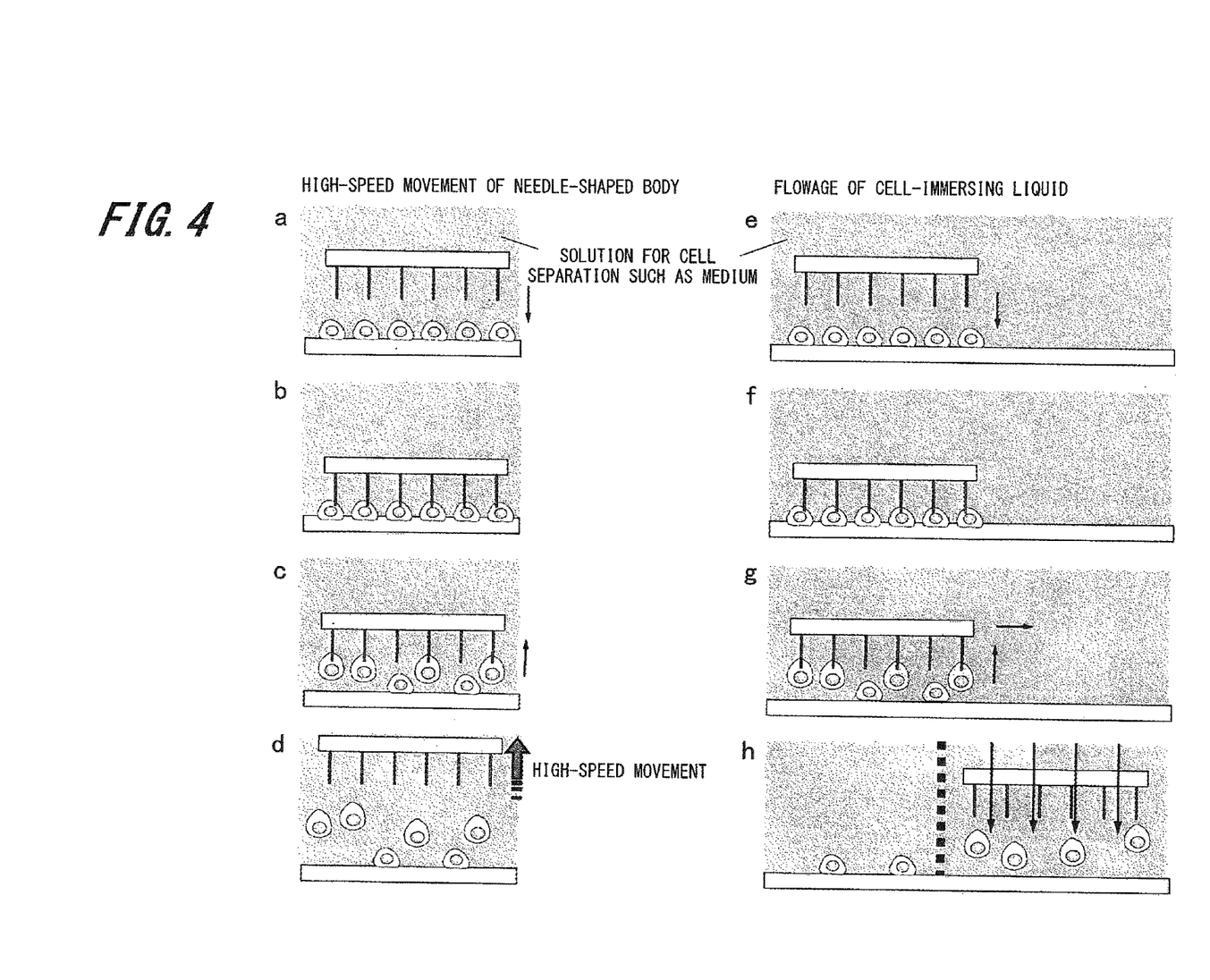
FIG. 4 illustrates a process of recovering cells into a liquid.

Now, description is made with respect to a cell separation apparatus of the present invention and an operation of discriminating and separating cells using the cell separation apparatus, referring to FIG. 3 and FIG. 4.

The cell separation apparatus of the present invention includes a cell observation device 2, a two-dimensional stage 3 provided to the cell observation device 2, a micro-contact device 1, a needle-shaped-body-arrayed device 4 on which a sufficient amount of the marker-binding substance specific to a target cell has been immobilized, mounted on the micro-contact device 1 and positioned above the two-dimensional stage 3, a substrate-accommodating container 5 arranged on the two-dimensional stage 3, a cell array substrate 6 having cells arranged on its surface, and a cell recovery substrate 7. The cell array substrate 6 and the cell recovery substrate 7 are arranged in the substrate-accommodating container 5 so as to be adjacent to each other. The needle-shaped bodies on which marker-binding substances have been immobilized are configured to be movable upward and downward (FIG. 3) by a moving device and a position control device (both not shown in figure) for the needle-shaped-body-arrayed device 4. The position control device is capable of controlling the upward and downward moving speed of the needle-shaped-body-arrayed device 4 provided with the needle-shaped bodies, and includes a dwell time controlling device configured to control a position-holding time of the needle-shaped-body-arrayed device 4 provided with the needle-shaped bodies at a lowered position. The force applied to the needle-shaped-body-arrayed device 4 is detected by the micro-contact device 1, and thereby the needle-shaped bodies are prevented from being broken.

The adhesion forces of the cells on the cell array substrate 6 have been decreased by the above-described cell-substrate adhesion force decreasing means.

The operation of discriminating and separating cells using the present apparatus is illustrated in (a) through (f) of FIG. 3. The gray parts in figures represent liquid. In the present invention, for example, first, the cell array substrate 6 having cells on its surface are arranged adjacent to the cell recovery substrate 7, in the substrate-accommodating container 5 filled with a liquid, and the substrate-accommodating container 5 is placed on the two-dimensional stage 3 of the present apparatus. Then, while monitoring with the cell observation device 2, the two-dimensional stage 3 is manipulated such that the needle-shaped bodies of the needle-shaped-body-arrayed device 4 come right above the cells on the cell array substrate 6, then, while monitoring contact pressure of the needle-shaped-body-arrayed device 4, the needle-shaped-body-arrayed device 4 is gradually moved closer to the cell array substrate 6, thereby causing the needle-shaped bodies to be inserted into the cells, respectively. The needle-shaped-body-array device 4 with the needle-shaped bodies is held in this state for a predetermined period of time by the dwell time controlling device, and the binding reactions of the marker-binding substances immobilized on the needle-shaped bodies and the target marker substances are carried out.

Subsequently, the needle-shaped-body-arrayed device 4 with the needle-shaped bodies is moved upward, thereby pulling up cells and separating the cells from the cell array substrate 6. The separated cells are cells each having the target marker substance inside, and are detached from the needle-shaped bodies and recovered by bringing the cells into contact with the cell recovery substrate 7 and pulling-up the needle-shaped-body-arrayed device 4.

As the cell recovery substrate 7, for example, the above-described BAM-immobilized substrate in which BAM molecular density has been controlled to show a cell adhesion force of 30 nN or above, or the above-described small orifice arrayed substrate with a suction pressure controlling means may be cited. In FIG. 3, (a) through (e) illustrate an outline of the operation when the above-described BAM-immobilized substrate whose BAM molecular density has been controlled is used, and in FIG. 3, (f) illustrates the case of using the small orifice arrayed substrate having the suction pressure controlling means.

In FIG. 3, the cell recovery substrate 7 (small orifice arrayed substrate) shown in (f) is provided with a liquid suction device such as a pump, etc., and the suction pressure thereof is adjustable. In this case, cells are detached from the needle-shaped bodies by the liquid suction force from small orifices of the small orifice arrayed substrate, and recovered on the small orifice arrayed substrate.

The BAM-immobilized substrate or the small orifice arrayed substrate having a suction pressure controlling means may be used not only as a cell recovery substrate but also as a substrate for first arraying cells that are to be separated with the needle-shaped bodies. These substrates are effective in cases in which the adhesion forces of cells to a substrate decrease too much due to trypsin treatment, etc., the cells are released in a liquid, resulting in that positioning of the needle-shaped bodies relative to the cells becomes difficult.

In the present apparatus, it is possible to provide another device as the cell recovery device, for example, a moving device to move the needle-shaped bodies at a high speed in a liquid ((a) through (d) of FIG. 4), or a device to generate a liquid flow toward the needle-shaped bodies.

The former moving device moves the needle-shaped bodies holding pulled-up cells to a cell recovering position within the substrate accommodating container 5, and causes the pulled-up cells to be detached from the needle-shaped bodies by moving the needle-shaped bodies at a high speed in the liquid. The moving direction of the needle-shaped bodies is not limited in particular. The needle-shaped-body-arrayed device 4 with the needle-shaped bodies is configured such that the upward and downward moving speed when pulling up cells can be controlled, as described above, and it is possible to elevate the needle-shaped bodies at a high speed using this moving device. In this case, the moving speed can be made adjustable in a range exceeding the above-described cell pulling-up speed of 1-500 µm/sec.

The latter device detaches pulled-up cells by causing the pulled-up cells to contact the fluidized liquid. As illustrated in (e) through (h) of FIG. 4, for example, a liquid flow flowing downward from above is generated at the cell recovering position, and by causing the needle-shaped bodies that have pulled up cells to contact the liquid flow, the cells are detached from the needle-shaped bodies. The speed of the liquid flow also may be made adjustable accordingly.

When these cell recovery devices are used, recovered cells are in floating conditions in the liquid, and it is possible to recover the cells together with the liquid. In this case, the corresponding relationships between the recovered cells and respective cells on the cell array substrate 6 before being separated cannot be grasped, however, separated cells have same property that in each of which the same marker substance is present. Therefore, such cell recovery devices are preferable ones, for example, in a case that it is sufficient if a cell in which a specific marker substance is present can be separated from varieties of cells. In the above-described example, even if the substrate is a culture vessel, the condition of recovering cells can be observed in real time by the cell observation device 2.

In the present invention, while using any of the above-described cell recovery devices and the cell array substrate on which cells are arrayed in large quantity, multiple needle-shaped bodies on which marker-binding substances have been immobilized respectively are provided in order to selectively separate target cells at the same time among from multiple cells as discriminating and separating objects, however, with respect to the shape of the cell array, designs according to needs, such as the one-dimensionally arrayed one, the two-dimensionally arrayed one, etc., may be prepared.

Below, an embodiment of the present invention is described, however, the present invention is not limited by the embodiment.

In the present embodiment, an example is illustrated, in which an anti-nestin antibody has been immobilized on an AFM probe (ATEC-CONT by NanoWorld AG) that had been etched so as to have the diameter of 200 nm, and using this antibody-immobilized nanoneedle (AFM probe), a mouse embryonic carcinoma cell 19, which is a nestin-positive cell, has been mechanically separated. An AFM probe and an AFM device as shown in FIG. 1 are used, so that it is a case that single needle-shaped body is used.

The adhesion force was measured by detaching a cell from a substrate in a perpendicular direction using the AFM probe that has been etched in a hook shape. The adhesion force of a P19 cell cultured on an ordinary plastic dish was 25±15 nN. The adhesion force of a mouse fibroblast cell NIH3T3 used as a nestin-negative cell was the same. In order to induce differentiation of the mouse P19 cell to a nerve cell, $1\times10^5$ of P19 cell were suspended in 10 ml of α-MEM containing 10% FBS, GA, GlutaMAX, and 1 µM retinoic acid, and suspension culture was carried out 4 days. Cells recovered by spontaneous precipitation were dissociated by trypsin/EDTA, disseminated to a glass-base dish which was treated with 0.02% polyethylenimine for one hour in a room temperature, and cultured 5-10 days, and the cells thus obtained were used for experiments.

The nanoneedle was prepared by etching a probe (ATEC-CONT) made of a single-crystal silicon (spring constant: 0.07 N/m), with a focused ion beam, so as to have the diameter of 200 nm and the length of 10 µm. The anti-nestin antibody was immobilized on the nanoneedle by immersing the nanoneedle for one minute in a room temperature in a 0.5% MPC polymer (2-methacyloyloxyethyl phosphoryl choline (MPC), γ-methacryloxypropyl trimethoxy silane (MPTS), p-nitrophenyloxycarbonyl poly(oxyethylene) methacrylate (MEONP)=7:1:2), drying it at 70° C. for 6 hours, and immersing it in a 180 nM anti-nestin antibody or anti-neurofilament antibody.

The operation of inserting the nanoneedle on which the anti-nestin antibody or the anti-neurofilament antibody has been immobilized into a cell and pulling up the cell was carried out using NanoWizard I (JPK Instruments AG). The insertion operation was carried out 10 times for each cell, with the insertion speed of the nanoneedle at 6 µm/sec (loading rate: 0.4 µN/sec) and the dwell time at 1 second.

With respect to cultured cells with no treatment, the rupture force when withdrawing the nanoneedle on which an antibody has been immobilized was measured. Force curves which are obtained when the nanoneedle is inserted into a cell are shown in the middle of FIG. 1 (the upper part: P19 cell, the lower part: NIH3T3 cell). When the nanoneedle penetrates through a cell membrane in the insertion process, a steep relaxation of a repulsive force (repulsive force drop) is observed in the force curve. It is known that when a repulsive force drop is observed, the nanoneedle has been certainly inserted into the cell. If the nanoneedle on which an antibody has been immobilized is inserted into a cell, an antigen-antibody complex is formed within the cell, and the binding is broken by the withdrawal operation. The magnitude of interaction can be observed as the attractive force that is below a baseline, and the maximum value thereof was analyzed as the rupture force of binding. Values of the rupture forces when the insertion operation of the nanoneedle on which an anti-nestin antibody has been immobilized was carried out to P19 cells and NIH3T3 cells are plotted in the right side part of FIG. 1. In each of columns separated from each other by dotted lines, force detection data with respect to individual cells are shown, and all of the data obtained by the operation of repeatedly inserting the nanoneedle 10 times are plotted in each column. A clear difference is seen in the values of rupture forces of P19 cells and NIH3T3 cells as indicated by plotted data. In P19 cells differentiated into neural cells showing morphology specific to neural cells such as dendrite elongation, etc., a noticeable rupture force was not recognized as in NIH3T3 cells. These differentiated cells were confirmed as nestin-negative, as a result of immunostaining.

Further, from the result above, it was found that when a force threshold value is equivalent to the average value plus four standard deviations of the force detected in NIH3T3 cells, all NIH3T3 cells are judged as nestin-negative cells. This value varies depending on the antibody-immobilizing amount and the type of cells, and is about 500 pN or below. In contrast, according to the measurement result of P19 cells, the rupture force of 1 nN or larger was detected at least one time with respect to all of the cells, and the rupture force of 2 nN or larger was observed in 4 pieces out of 5 pieces. Five independent experiments were carried out, and similar tendencies were observed. Therefore, the adhesion force between cells and the substrate when performing the operation of mechanically pulling up and separating each cell while targeting a nestin was controlled to 500 pN or above and 2 nN or below.

With respect to cultured P19 cells, it was possible to decrease the adhesion force to about 2 nN by treating them 10 minutes by PBS containing trypsin of 0.01% final concentration. The above-described nanoneedle on which an anti-nestin antibody has been immobilized was inserted into each P19 cell treated with trypsin, and the pulling-up operation was carried out, resulting in that it was possible to pull up almost all the cells during ten insertion operations. In contrast, when the similar operation was carried out with respect to NIH3T3 cells or P19 cells which have undergone differentiation induction to neural cells and have become nestin-negative, no cell was pulled up.

Subsequently, a substrate for recovering pulled-up cells was prepared. By causing BAM (SUNBRIGHT 0E-040CS by NOF CORPORATION) adjusted to various densities to react for 60 minutes on substrates on each of which BSA has been immobilized, BAM-immobilized substrates were prepared. A P19 cell separated by trypsin was forcibly brought into contact with each substrate with a hook-shaped AFM probe, and then immediately the pulling-up operation was performed, and thereby the adhesion force of a cell was measured. As a result of experiments, the adhesion-breaking force of 35 nN was observed with respect to the substrate treated by BAM of 1 μM, and it was confirmed that such substrate suffices as the substrate for recovering cells. The BM-modified substrate for recovering cells was settled in a substrate-accommodating container, a cell subjected to a pulling-up operation with the nanoneedle modified by an anti-nestin antibody was brought into contact with the substrate, and then, the nanoneedle was pulled up, and thereby the cell was recovered on the BM-modified substrate. With this operation, it was possible to recover 30 cells continuously.

The invention claimed is:

1. A cell separation method of selectively separating only target cells in cell samples on a first substrate, each target cell containing a marker substance, the cell separation method comprising steps of:

inserting a needle-shaped body, on which a substance that selectively binds to the marker substance within each target cell has been immobilized, into each of the cell samples on the first substrate, thereby causing the marker substance within each target cell in the cell samples to bind to the needle-shaped body through the immobilized substance that selectively binds to the marker substance, and then pulling up the needle-shaped body; and making a binding force between the needle-shaped body and each target cell in the cell samples on the first substrate when the needle-shaped body has been inserted into the target cell and the marker substance within the target cell has bound to the needle-shaped body greater than an adhesion force between the first substrate and each of the cell samples on the first substrate, wherein in the step of making the binding force between the needle-shaped body and each target cell in the cell samples when the needle-shaped body has been inserted into the target cell and the marker substance within the target cell has bound to the needle-shaped body greater than the adhesion force between the first substrate and each of the cell samples on the first substrate, the adhesion force between the first substrate and each of the cell samples on the first substrate is adjusted such that an adhesion force is within 500 pN-2 nN when a loading rate of the needle-shaped body, on which the substance that selectively binds to the marker substance within each target cell has been immobilized, into each of the cell samples on the first substrate is 0.4 μN/sec.

2. The cell separation method according to claim 1, wherein in the step of making the binding force between the needle-shaped body and each target cell in the cell samples when the needle-shaped body has been inserted into the target cell and the marker substance within the target cell has bound to the needle-shaped body greater than the adhesion force between the first substrate and each of the cell samples on the first substrate, the binding force between the needle-shaped body and each target cell in the cell samples when the needle-shaped body has been inserted into the target cell and the marker substance within the target cell has bound to the needle-shaped body is made greater than the adhesion force between the first substrate and each of the cell samples on the first substrate by increasing the binding force between the needle-shaped body and each target cell when the needle-shaped body has been inserted into the target cell and the marker substance within the target cell has bound to the needle-shaped body and/or by decreasing the adhesion force between the first substrate and each of the cell samples on the first substrate.

3. The cell separation method according to claim 2, wherein in the step of making the binding force between the needle-shaped body and each target cell in the cell samples when the needle-shaped body has been inserted into the target cell and the marker substance within the target cell has bound to the needle-shaped body greater than the adhesion force between the first substrate and each of the cell samples on the first substrate, the binding force between the needle-shaped body and each target cell in the cell samples when the needle-shaped body has been inserted into the target cell and the marker substance within the target cell has bound to the needle-shaped body is made greater than the adhesion force between the first substrate and each of the cell samples on the first substrate by controlling the needle-shaped body to a shape that increases a contact area of the marker substance and the needle-shaped body within each target cell when the needle-shaped body has been inserted into the target cell and/or by controlling a dwell time of the needle-shaped body within each of the cell samples when the needle-shaped body has been inserted into the cell sample.

4. The cell separation method according to claim 3, wherein the needle-shaped body, on which the substance that selectively binds to the marker substance within each target cell has been immobilized, is in a cylindrical shape with an aspect ratio of 50 or above and a diameter of 300 nm or below.

5. The cell separation method according to claim 3, wherein in the step of inserting the needle-shaped body, on which the substance that selectively binds to the marker substance within each target cell has been immobilized, into each of the cell samples on the first substrate and pulling up the needle-shaped body, the dwell time within each of the cell samples of the needle-shaped body, on which the substance that selectively binds to the marker substance within each target cell has been immobilized, is 1-10 sec.

6. The cell separation method according to claim 2, wherein in the step of making the binding force between the needle-shaped body and each target cell in the cell samples when the needle-shaped body has been inserted into the target cell and the marker substance within the target cell has bound to the needle-shaped body greater than the adhesion force between the first substrate and each of the cell samples on the first substrate, the binding force between the needle-shaped body and each target cell in the cell samples when the needle-shaped body has been inserted into the target cell and the marker substance within the target cell has bound to the needle-shaped body is made greater than the adhesion force between the first substrate and each of the cell samples on the first substrate by decreasing the adhesion force between the first substrate and each of the cell samples by treatment of the cell samples with a proteolytic enzyme and/or treatment of the cell samples with an adhesion protein expression inhibitor.

7. The cell separation method according to claim 1, the cell separation method further comprising any one or more of:
   controlling density of a cell adhesion material to be immobilized on the first substrate;
   controlling a suction power when suction immobilizing the cell samples on the first substrate; and
   controlling each cell contact area of chambers provided in the first substrate for holding the cell samples.

8. The cell separation method according to claim 1, the step of inserting the needle-shaped body, on which the substance that selectively binds to the marker substance within each target cell has been immobilized, into each of the cell samples on the first substrate and pulling up the needle-shaped body includes controlling a speed of pulling up the needle-shaped body and/or controlling a position of insertion and a frequency of insertion of the needle-shaped body into each cell sample.

9. The cell separation method according to claim 8, wherein in the step of inserting the needle-shaped body, on which the substance that selectively binds to the marker substance within each target cell has been immobilized, into each of the cell samples on the first substrate and pulling up the needle-shaped body, the speed of pulling up the needle-shaped body is 1-500 μm/sec.

10. The cell separation method according to claim 8, wherein in the step of inserting the needle-shaped body, on which the substance that selectively binds to the marker substance within each target cell has been immobilized, into each of the cell samples on the first substrate and pulling up the needle-shaped body, the insertion position of the needle-shaped body into a same cell sample is changed each time the needle-shaped body is inserted into the cell sample, and the frequency of insertion of the needle-shaped body into a same cell sample is 3-10 times.

11. A cell recovery method of recovering target cells each pulled up by a needle-shaped body with the cell separation method according to claim 1, the cell recovery method comprising:
   causing each of the target cells pulled up by a needle-shaped body to contact a second substrate and then pulling up the needle-shaped body, thereby causing the pulled-up target cell to be separated from the needle-shaped body and recovered to the second substrate; and
   making an adhesion force of each of the pulled-up target cells to the second substrate greater than a binding force between the needle-shaped body and the pulled-up target cell.

12. The cell recovery method according to claim 11, further comprising any one or more of:
   controlling a contact time of each pulled-up target cell relative to the second substrate;
   controlling density of a cell adhesion material to be immobilized on the second substrate;
   controlling a suction power when suction immobilizing each pulled-up target cell on the second substrate; and
   controlling each cell contact area of chambers provided in the second substrate for holding recovered target cells.

13. A cell recovery method of recovering target cells, each pulled up by a needle-shaped body with the cell separation method according to claim 1, in a liquid by increasing resistance of the liquid relative to each pulled-up target cell, thereby causing each pulled-up target cell to drop from the needle-shaped body and recovering the pulled-up target cell in the liquid, the cell recovery method comprising:
   moving the needle-shaped body holding each pulled-up target cell in a liquid at a speed high enough to dislodge the cell from the needle-shaped body;
   and/or
   causing the needle-shaped body holding each pulled-up target cell to contact a flowing liquid.

14. The cell separation or recovery method according to claim 1, wherein a plurality of the needle-shaped bodies, on each of which the substance that selectively binds to the marker substance within each target cell has been immobilized, are arrayed, and respective needle-shaped bodies are individually inserted into the cell samples at the same time.

* * * * *